US012187661B2

(12) United States Patent
Brogden et al.

(10) Patent No.: US 12,187,661 B2
(45) Date of Patent: Jan. 7, 2025

(54) METHODOLOGIES TO PRODUCE SIMULANTS OF TEXTURED THREAT COMPOUNDS

(71) Applicant: The Government of the United States of America, as represented by the Secretary of Homeland Security, Washington, DC (US)

(72) Inventors: Michael Brogden, Galloway, NJ (US); Kevin Pedersen, Atco, NJ (US); Ronald Krauss, Galloway, NJ (US)

(73) Assignee: The Government of the United States of America, as represented by the Secretary of Homeland Security, Washington, DC (US)

(*) Notice: Subject to any disclaimer, the term of this patent is extended or adjusted under 35 U.S.C. 154(b) by 5 days.

(21) Appl. No.: 18/109,007

(22) Filed: Feb. 13, 2023

(65) Prior Publication Data

US 2023/0202943 A1 Jun. 29, 2023

Related U.S. Application Data

(62) Division of application No. 16/230,308, filed on Dec. 21, 2018, now abandoned.
(Continued)

(51) Int. Cl.
*C06B 45/06* (2006.01)
*C06B 21/00* (2006.01)
(Continued)

(52) U.S. Cl.
CPC .......... *C06B 45/06* (2013.01); *C06B 21/0041* (2013.01); *C06B 21/005* (2013.01);
(Continued)

(58) Field of Classification Search
None
See application file for complete search history.

(56) References Cited

U.S. PATENT DOCUMENTS 5,958,299 A 9/1999 Kury et al.
8,563,316 B2 10/2013 Duffy et al.
(Continued)

OTHER PUBLICATIONS

Smith, J.A. et al., "Case for an Improved Effective-Atomic-Number for the Electronic Baggage Scanning Program," Lawrence Livermore National Laboratory, (2011) https://www.osti.gov/biblio/1033743.
(Continued)

*Primary Examiner* — Aileen B Felton
(74) *Attorney, Agent, or Firm* — Lavanya Ratnam; Robert W. Busby; Kelly G. Hyndman

(57) ABSTRACT

Various embodiments of the present invention are directed towards a simulant and method relating to producing a simulant. For example, a simulant of a textured target threat includes a background material associated with a background attenuation, and a texture component(s) dispersed in the background material and associated with a component attenuation and a component characteristic. The component characteristic prevents the component attenuation of the texture component from being homogeneously dispersed throughout the background attenuation of the background material, to cause the simulant to mimic an aspect(s) of an X-ray signature of the textured target threat.

6 Claims, 6 Drawing Sheets

Related U.S. Application Data

(60) Provisional application No. 62/608,940, filed on Dec. 21, 2017.

(51) Int. Cl.
*C06B 23/00* (2006.01)
*C06B 45/02* (2006.01)
*C06B 45/04* (2006.01)
*G01N 33/22* (2006.01)

(52) U.S. Cl.
CPC .......... *C06B 21/0066* (2013.01); *C06B 45/02* (2013.01); *C06B 45/04* (2013.01); *C06B 23/00* (2013.01); *G01N 33/227* (2013.01)

(56) References Cited

U.S. PATENT DOCUMENTS

| | | | |
|---|---|---|---|
| 2009/0194744 A1* | 8/2009 | Adebimpe | F41H 11/134 252/408.1 |
| 2013/0026420 A1* | 1/2013 | Duffy | C06B 23/00 252/408.1 |
| 2015/0268016 A1* | 9/2015 | Eshetu | F42B 8/00 434/11 |

OTHER PUBLICATIONS

Azevedo, S.G., et al., "System-Independent Characterization of Materials Using Dual-Energy Computed Tomography," IEEE Transactions on Nuclear Science, vol. 63, No. 1, pp. 341-350(Feb. 2016, doi: 10.1109/TNS.2016.2514364.

Cullen, D.E. et al., "The 1989 Livermore Evaluated Photon Data Library (EPDL)," UCRL-ID-103424, Lawrence Livermore National Laboratory, Mar. 1, 1990.

Cullen, D.E., et al., "The Evaluated Photon Data Library '97 Version," UCRL-LR-50400, vol. 6, Rev. 5, Lawrence Livermore National Laboratory Sep. 19, 1997.

Hubbell, J.H., et al, "Tables of X-Ray Mass Attenuation Coefficients and Mass Energy-Absorption Coefficients from 1 keV to 20 MeV for Elements z = 1 to 92 and 48 Additional Substances of Dosimetric Interest," NISTIR 5632, 1996 http://www.nist.gov/pml/data/xraycoef/index.cfm.

Bond, K. C., et.el., "ZeCalc Algorithm Details", Version 6, Lawrence Livermore National Laboratory Tech. Rep., LLNL-TR-609327, Jan. 3, 2013.

\* cited by examiner

METHODOLOGIES TO PRODUCE SIMULANTS OF TEXTURED THREAT COMPOUNDS

CROSS-REFERENCE TO RELATED APPLICATIONS

This application is a divisional of U.S. patent application Ser. No. 16/230,308 filed Dec. 21, 2018, entitled "Methodology for Developing Texture in Simulants," which claims the benefit of U.S. Provisional Application No. 62/608,940 entitled "Methodology for Developing Texture in Simulants," filed on Dec. 21, 2017, the contents of which are incorporated herein by reference in their entireties.

STATEMENT OF GOVERNMENT INTEREST

The present invention was made by one or more employees of the United States Department of Homeland Security in the performance of official duties. The Government has certain rights in the invention.

FIELD

The present invention relates generally to the field of simulants, and more specifically to the field of simulants to serve as surrogates to hazardous threats and explosives for training and testing.

BACKGROUND

Simulants are needed for both training and testing explosive detection systems (EDSs) and advanced imaging technology (AIT) portals, as well as for training and testing security personnel. The simulants are used in place of live explosives in locations where live explosives cannot be used due to safety concerns. Simulants are manufactured to produce the same detector response as live threats, but as technology improves, more measurable properties may be needed for a given simulant to match a specific threat.

For example, simulants have been designed for X-ray imaging explosive detection system (EDS) platforms where only the explosive's X-ray properties were matched, and only the averages of those properties. However, in recent years there has been a focus on developing simulants that better match the physical morphology of the threat. Characteristics such as flexibility, compressibility, and particle size have been studied in recent years with some success.

SUMMARY

In an example embodiment, a simulant of a textured target threat includes a background material associated with a background attenuation; and a first texture component dispersed in the background material and associated with a first component attenuation and a first component characteristic. The first component characteristic prevents the first component attenuation of the first texture component from being homogeneously dispersed throughout the background attenuation of the background material, to cause the simulant to mimic a first aspect of an X-ray signature of the textured target threat.

In another example embodiment, a method of producing a simulant of a textured threat compound includes formulating a background material associated with a background attenuation; formulating a first texture component associated with a first component attenuation and a first component characteristic based on mechanically separating the first texture component according to the first component characteristic; and dispersing, in the background material, the first texture component. The first component characteristic enables dispersion of the first texture component in the background material of the simulant to mimic a first aspect of an X-ray signature of the textured target threat.

In yet another example embodiment, a method of producing a simulant of a textured threat compound includes quantitatively characterizing a threat texture of the textured threat compound; formulating a background material associated with a background attenuation; formulating a first texture component associated with a first component attenuation and a first component characteristic; dispersing, in the background material, the first texture component; quantitatively characterizing a simulant texture of the simulant; comparing the simulant texture to the threat texture; and iteratively adjusting the first texture component to cause the simulant texture to match the threat texture.

Other features and aspects will become apparent from the following detailed description, which taken in conjunction with the accompanying drawings illustrate, by way of example, the features in accordance with embodiments. This summary is not intended to identify key or essential features of the claimed subject matter, nor is it intended to limit the scope of the invention, which is defined solely by the claims attached hereto.

BRIEF DESCRIPTION OF THE DRAWINGS

One or more example embodiments are described in detail with reference to the following drawings. These drawings are provided to facilitate understanding and should not be read as limiting the breadth, scope, or applicability of the embodiments. For purposes of clarity and ease of illustration, these drawings are not necessarily made to scale.

Figure 1:
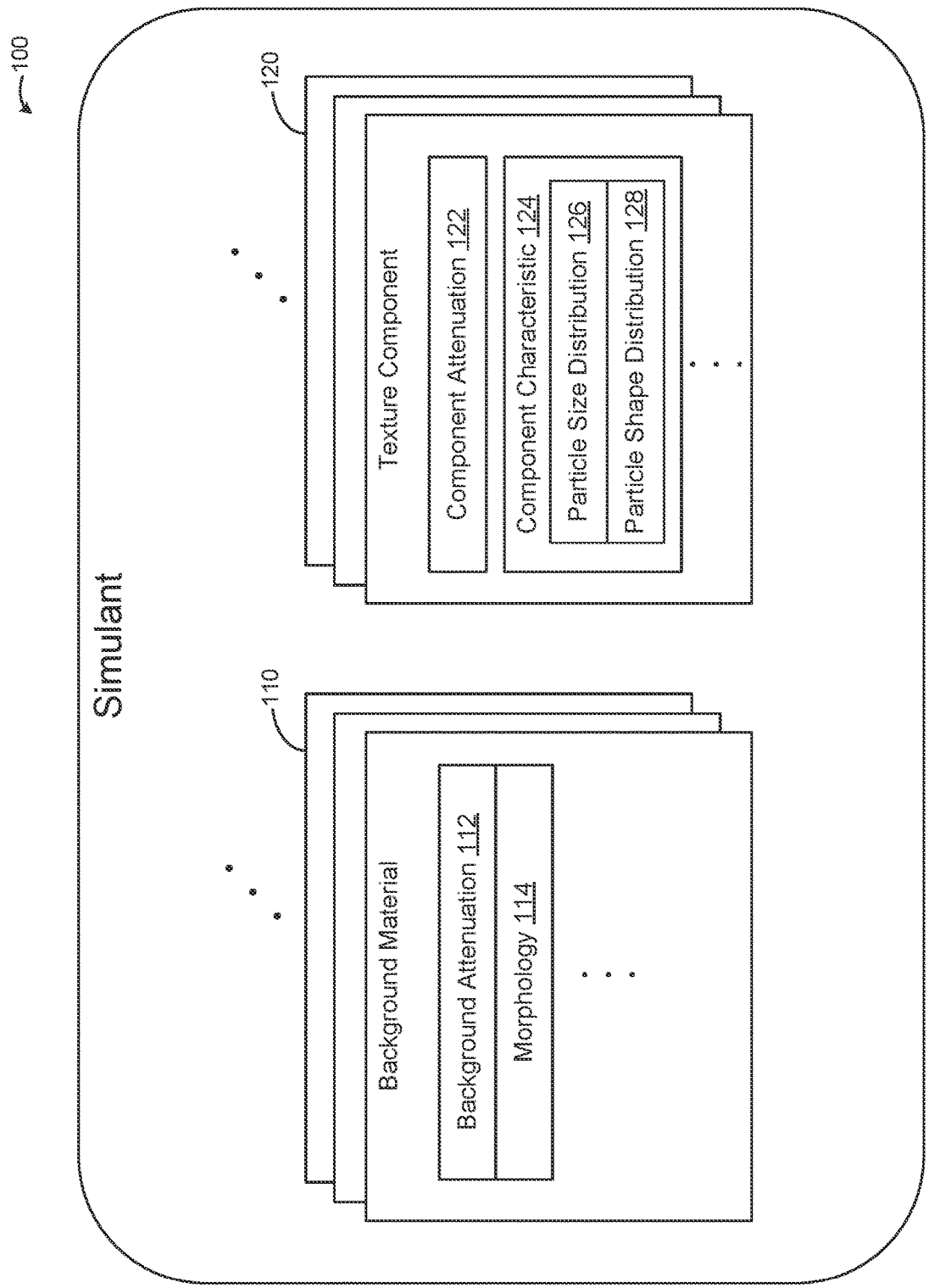
FIG. 1 illustrates a simulant of a textured target threat according to an example embodiment.

These drawings are not intended to be exhaustive or to limit the invention to the precise form(s) disclosed. It should be understood that the present invention can be practiced with modification and alteration, and that the invention is limited only by the claims and the equivalents thereof.

DETAILED DESCRIPTION

Example embodiments described herein relate to developing and manufacturing explosive simulants having textured components. The simulants can be used as surrogates to explosive threats for training and testing on explosive detection systems (EDS) and advanced imaging technology (AIT) portals. Designing simulants can involve matching intrinsic properties of a threat as detected by a given technology. For X-ray EDS, these properties include mass density (ρ), effective atomic number (Z-effective), and electron density, which is highly correlated to computed tomography (CT) number. However, as EDS technology advances, higher spatial resolution images are being acquired, which provides the opportunity for performing a more rigorous characterization of the threat. The outcome of the analysis is that the texture of the threat as revealed in X-ray images can be quantitatively characterized, resulting in an additional aspect of the threat that can be incorporated into the development of a simulant.

With advances in EDS imaging technology, EDS are achieving the ability to distinguish and potentially detect texture within objects. For example, explosive detection systems can have varying degrees of image resolution, and as technology advances the spatial resolution of these systems is improving. Higher resolution EDS may be capable of identifying and detecting inhomogeneous texture within a given image or object. Furthermore, because some homemade explosives are known to contain significant texture that is visible to the human eye in X-ray images, simulants with such texture are needed to adequately train security personnel.

Some explosive threats are heterogeneous and contain texture or other identifiable components within the base material. If a given threat is known to contain texture that can be identified on an EDS or other type of scanner, then that component must be quantitatively characterized and reproduced in the simulant. Depending on the image resolution of the EDS, the acquired images may be used to identify the texture components. Positive identification of the texture in a threat may result in increased explosive detection performance, or may potentially decrease false positives. At the very least, the identification of texture within an object could initiate an alarm resolution procedure resulting in the object going through additional analysis.

If a threat contains identifiable texture then that characteristic should be reproduced in a simulant, otherwise the simulant doesn't accurately portray the identifiable feature set of the threat. Failure to fully represent the threat's characteristics in the simulant may result in detection failures by screeners or detection algorithms.

Example approaches can be used to measure, model, and reproduce the effects of a range of attenuating particles found in explosive threats that contribute to threat texture, e.g., by identifying and matching crystal or particle texture within the threat, and reproducing threat characteristics and/or textures that are spatially variant (e.g., non-homogeneously dispersed). Additionally, threat characteristics can be quantified based on average properties as measured by EDS or other type of scanner (such as a scanner to obtain micro-CT images), including average density, Z-effective, and X-ray attenuation properties. Example simulants also can be produced to match the threat morphology in terms of solid, semisolid, powder, or liquid. Thus, example approaches can characterize an explosive threat's internal identifiable texture and expanding the explosive-simulant development approach to include and match the texture components. Simulant formulations can be produced that contain attenuating particles similar to the threat, as verified using an X-ray micro-CT system. The simulant's texture component can be varied continuously such that the texture properties of the simulant spanned the range of texture properties measured from the threat material. Accordingly, a simulant developer or user can use the example approaches to combine different proportions of non-texture and texture components of the simulant to create a plurality of textures as needed to match a variety of threat(s) of interest.

Accordingly, the example approaches and embodiments described herein enable the development of a plurality of simulants that contain texture particles that can have a plurality of X-ray attenuation properties, using various methods described herein. The attenuation properties of the texture particles may be higher or lower than the background material, and the proportions may be varied continuously to match the texture properties of the threat.

FIG. 1 illustrates a simulant 100 of a textured target threat according to an example embodiment. The simulant 100 includes at least one background material 110 associated with a background attenuation 112 and morphology 114. The simulant 100 also includes at least one texture component 120 associated with a component attenuation 122 and a component characteristic 124. Example component characteristics 124 include particle size distribution 126, particle shape distribution 128, and other characteristics that, e.g., can prevent homogeneous dispersion of attenuation to mimic a textured aspect of an X-ray signature of a textured target threat.

Figure 2:
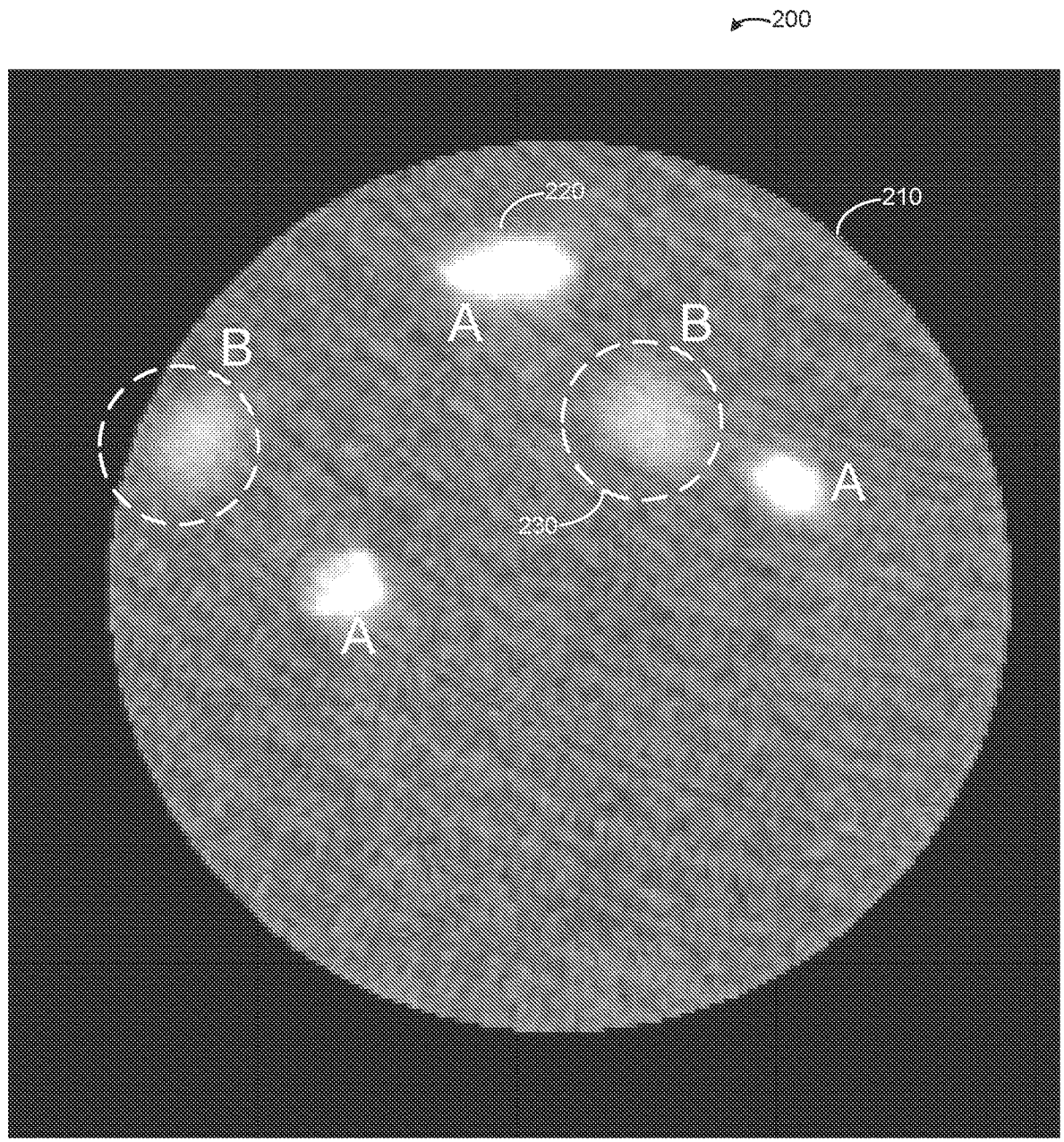
FIG. 2 illustrates a two-dimensional slice of a textured target threat material to be simulated by a simulant produced according to an example embodiment.

FIG. 2 illustrates a two-dimensional slice of a textured target threat material 200 to be simulated by a simulant produced according to an example embodiment. The threat 200 includes a background material 210, first texture component 220 associated with a first component attenuation, and a second texture component 230 associated with a second component attenuation.

Image texture can be portrayed as any feature within the image that is identifiably different from the background in the image. For example, air gaps within an object that are evident in an X-ray image is a form of texture. In addition, aggregates or crystals within a powdered material can result in image texture. Although there are many ways to calculate features derived from images that are defined as texture, the concept of texture is that there are irregularities within the sample with sufficient size and preponderance that it can be identified and used in explosive detection. Therefore, it is necessary to accurately identify and characterize texture within threat materials, and reproduce the same effect in a simulant.

A particular type of improvised threat was scanned for characterization, e.g., with a dual-energy microCT system (which can have much higher resolution than current and near-future EDS), providing excellent images for texture analysis. The reconstructed tomographic slices, such as the slice illustrated in FIG. 2, were found to contain bright pixels and objects 220, 230 that were distinguishable from the background material 210. Example particles range from approximately 200 microns (0.2 millimeter) up to approximately 5 mm, and depending on the type of threat, particles can potentially exceed 1 cm or higher.

MicroCT texture analysis revealed that this particular threat material contained two distinct types of particles 220, 230, associated with significantly different attenuation, identified by the brightness of texture in the images. These first and second texture components 220, 230 can be referred to as "low" and "high" attenuation texture for convenience, but the attenuation was still higher than the background 210 in the images in both cases. Low attenuation texture particles 230 were only slightly brighter than the background 210 of the material, whereas the high attenuating particles 220 were much brighter than the background 210. Both low and high texture components 220, 230 are identified in FIG. 2. The grayscale value of each texture piece was characterized on an eight bit scale with pixel values ranging from 0 to 255, or black to white, respectively.

Figure 3:
FIG. 3 illustrates a three-dimensional image of a textured target threat material to be simulated by a simulant produced according to an example embodiment.

FIG. 3 illustrates a three-dimensional image of a textured target threat material 300 to be simulated by a simulant produced according to an example embodiment. The image of FIG. 3 is representative of a stack of two-dimensional images, such as the image shown in FIG. 2.

for the threat and the simulant background material, detected using both the micro-CT and the commercial EDS. The difference between the simulant and threat was less than 3% for all features, serving as a confirmation of the validity of the formulated background material. As shown in Table 1 below, X-ray properties are shown, as derived from an example EDS system. CTN High and CTN Low represent high and low energy CT number from the EDS, respectively. Ze and Pe represent effective atomic number and electron density, respectively, derived from the EDS data.

TABLE 1

| Sample | Morphology | Grayscale (micro-CT) | CTN High | CTN Low | Ze | Pe (mol e-/cc) |
|---|---|---|---|---|---|---|
| Threat | Powder | 122 | 4152 | 4060 | 6.754 | 0.207 |
| Simulant Background | Powder | 119 | 4191 | 4140 | 6.764 | 0.211 |
| Difference | — | 3.00 | 39 | 80 | 0.010 | 0.004 |
| % | — | 2.52% | 0.93% | 1.93% | 0.15% | 1.90% |

The three-dimensional image is helpful for characterizing and/or quantifying the contrast of texture particles, as well as other component characteristics such as the size, number, shape, and distribution of component particles in the samples to be used for producing simulants. Two dimensional image slices were stacked together and reconstructed into a 3-dimensional image. Background pixels were removed from the image using thresholding (e.g., by setting the threshold to remove those pixels with a pixel value less than the lowest value of any texture component), resulting in a 3D image of the texture particles, as illustrated in FIG. 3. The texture was analyzed using 2D slice images (to obtain a cross-sectional size/shape/number distribution of texture particles), and the 3D image stack (to obtain texture particle distribution information for all three dimensions). The component characteristic features of interest included the average pixel contrast distribution and the particle size distribution, but also included features related to particle shape distribution and pixel contrast distribution, as well as corresponding values for such characteristics, separate from their distributions. The results of the analysis confirmed that the illustrated threat contained two distinctly different types of texture, differentiated by their average contrast. One group, referred to as low attenuating, had image grayscale values in the range of 145-165, while the second group, referred to as high attenuating, had grayscale values greater than 200. Using a set of images from twelve different specimens, it was evident that the size and shape of particles was somewhat random. While there was no particular particle shape that was preferentially evident, the particle size distribution was regarded as an important feature to adequately characterize and then match in the simulant, in addition to matching the attenuation properties of the low and high attenuation particles.

Figure 4:
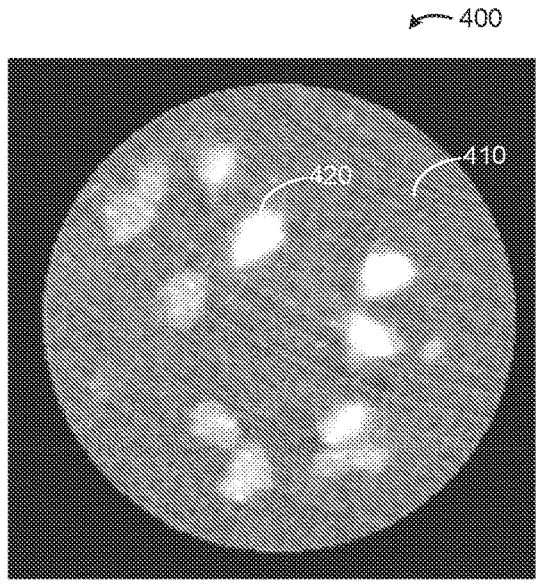
FIG. 4 illustrates a textured simulant according to an example embodiment.

FIG. 4 illustrates a textured simulant 400 according to an example embodiment. More specifically, the simulant 400 includes a plurality of first texture components 420, to provide high attenuating properties compared to the background material 410. To develop the simulant 400 that accurately represented the threat, the base morphology, average X-ray properties, and texture of the threat 400, had to be reproduced. First, a formulation was developed matching the morphology and X-ray properties of the threat's background 410. Table 1 provides the X-ray signature data Next, to create the high attenuation texture particles 420, a wax formulation was developed, melted, and cast into a solid block. The block was then broken apart, ground down, and sieved into various sizes of particles. A sample was prepared combining the background material 410 with the high attenuation particles 420 and scanned on the microCT for analysis. FIG. 4 illustrates this example of the resulting slice images containing high attenuating texture particles 420.

Figure 5:
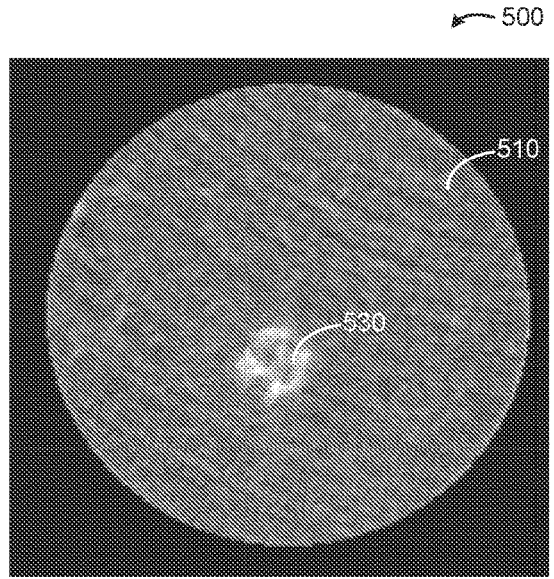
FIG. 5 illustrates a textured simulant according to another example embodiment.

FIG. 5 illustrates a textured simulant 500 according to another example embodiment. The simulant 500 represents the results of one example method, and see FIG. 6 below, illustrating the results of another example method. To develop low attenuating texture particles 530, two methods were explored. The first method of FIG. 5 used a high amount of wax binder (>80% by weight), mixed with a material having very low attenuation compared to the high attenuation components 420 of FIG. 4. The same melt-cast process, as described above and used to produce the high attenuating particles 420 in FIG. 4, was then applied on the low attenuation material to produce the low attenuation particle 530 in FIG. 5. The resulting particles 530 had an average grayscale value in the range of 180, which was too high to be used as a low attenuation particle when attempting to match this particular threat to be simulated. Furthermore, unlike that of the threat's low attenuating particles having relative and uniform particle characteristics, the simulant's low attenuating texture was irregular as illustrated in FIG. 5. A different approach was then used for simulating the low attenuation particles, as described below with reference to FIG. 6.

Figure 6:
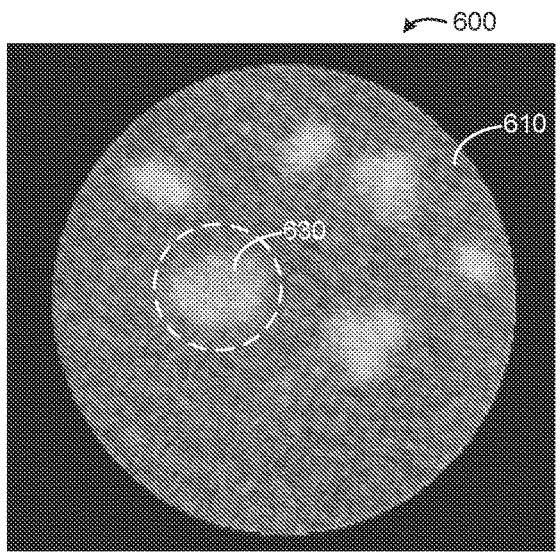
FIG. 6 illustrates a textured simulant according to yet another example embodiment.

FIG. 6 illustrates a textured simulant 600 according to yet another example embodiment. An alternative method was used for creating the illustrated low attenuating texture particles 630, which involved combining ground wax with the powdered background formulation 610 previously developed, in a 1:1 ratio by weight. The powders were then mixed together and aggregated by compression, which was achieved through vacuum suction. Once fused, the semi-solidified object was broken apart and sieved into varying mesh sizes. A sample was then prepared combining the background material 610 with these new particles and scanned on the microCT for analysis. The resulting low attenuating texture particles 630 had a grayscale in the range of 140-150, with an example slice as shown in FIG. 6. These results were then combined to mimic the texture of the threat as described below with reference to FIG. 7.

Figure 7:
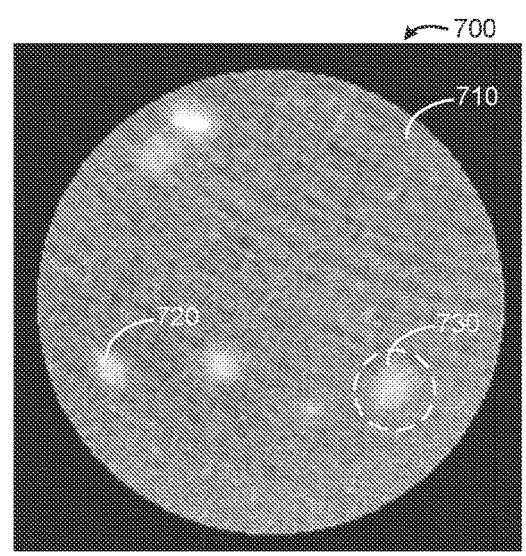
FIG. 7 illustrates a textured simulant according to yet another example embodiment.

FIG. 7 illustrates a textured simulant 700 according to yet another example embodiment. To create the simulant 700 that contains both the high and low attenuation texture components 720, 730, a formulation was developed that used the background material 710 (such as the previously-described background materials 410, 510, or 610) mixed with a proportion of high attenuating melt cast particles 720 (such as the previously-described particles 420) and low attenuating vacuum-fused aggregates 730 (such as the previously-described particles 630). The simulant 710 was scanned on the microCT for analysis and verification. FIG. 7 illustrates a cross-sectional slice of the combined texture simulant 700. The amount and size of each texture type 720, 730 was then adjusted as needed to match the internal texture makeup of the various threat specimens, e.g., based on characterizing various above-described component characteristics and/or distributions for the threat and sample, to ensure that they match within a desirable range corresponding to being generally visually indistinguishable when viewing scanning results. Characteristics of the simulant should match the threat at the appropriate spatial resolution level, e.g., as available on a given scanning machine and available state-of-the-art for scanning machines.

Figure 8:
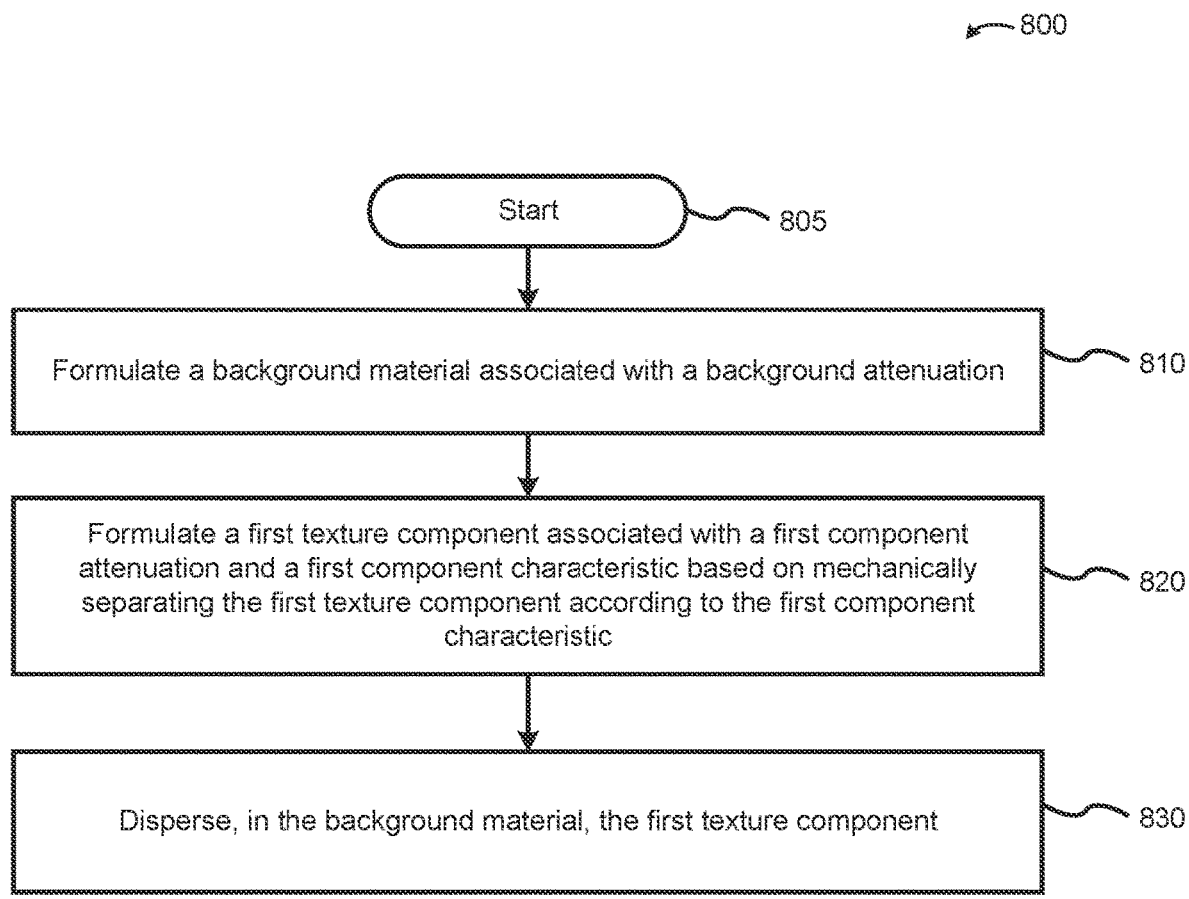
FIG. 8 illustrates a method of producing a simulant of a textured threat compound according to an example embodiment.

FIG. 8 illustrates a method 800 of producing a simulant of a textured threat compound according to an example embodiment. The method starts at block 805. In block 810, a background material associated with a background attenuation is formulated. For example, a background formulation was developed by producing a powder matching the morphology and X-ray properties of the threat's background.

In block 820 a first texture component associated with a first component attenuation and a first component characteristic is formulated based on mechanically separating the first texture component according to the first component characteristic. For example, the first texture component can be melted and cast, then broken up into various particle sizes, and separated into discrete size ranges by corresponding stages of sieves of varying mesh size, then combined in various proportions to achieve a desired size distribution. Other approaches include use specific techniques (sieve mesh shapes) for achieving particle shape distributions, or alternatives for casting the component ingredient before breaking it into particles (forming the ingredient into a sheet instead of a block, to achieve flake-shaped particles). For example, mechanical compression can be used to form granular texture, or to form a solid block that is then broken up in a manner similar to that used on a wax-based melt-cast block as described above. The texture component may or may not have a binder added. Such approaches can be different than a vacuum-based compression approach, in terms of how the compression is achieved.

In block 830, the first texture component is dispersed in the background material. For example, the texture component can be dispersed according to a component characteristic, to cause dispersion of the first texture component in the background material of the simulant to mimic a first aspect of an X-ray signature of the textured target threat, e.g., a variant/non-homogeneous distribution of the texture variations.

Figure 9:
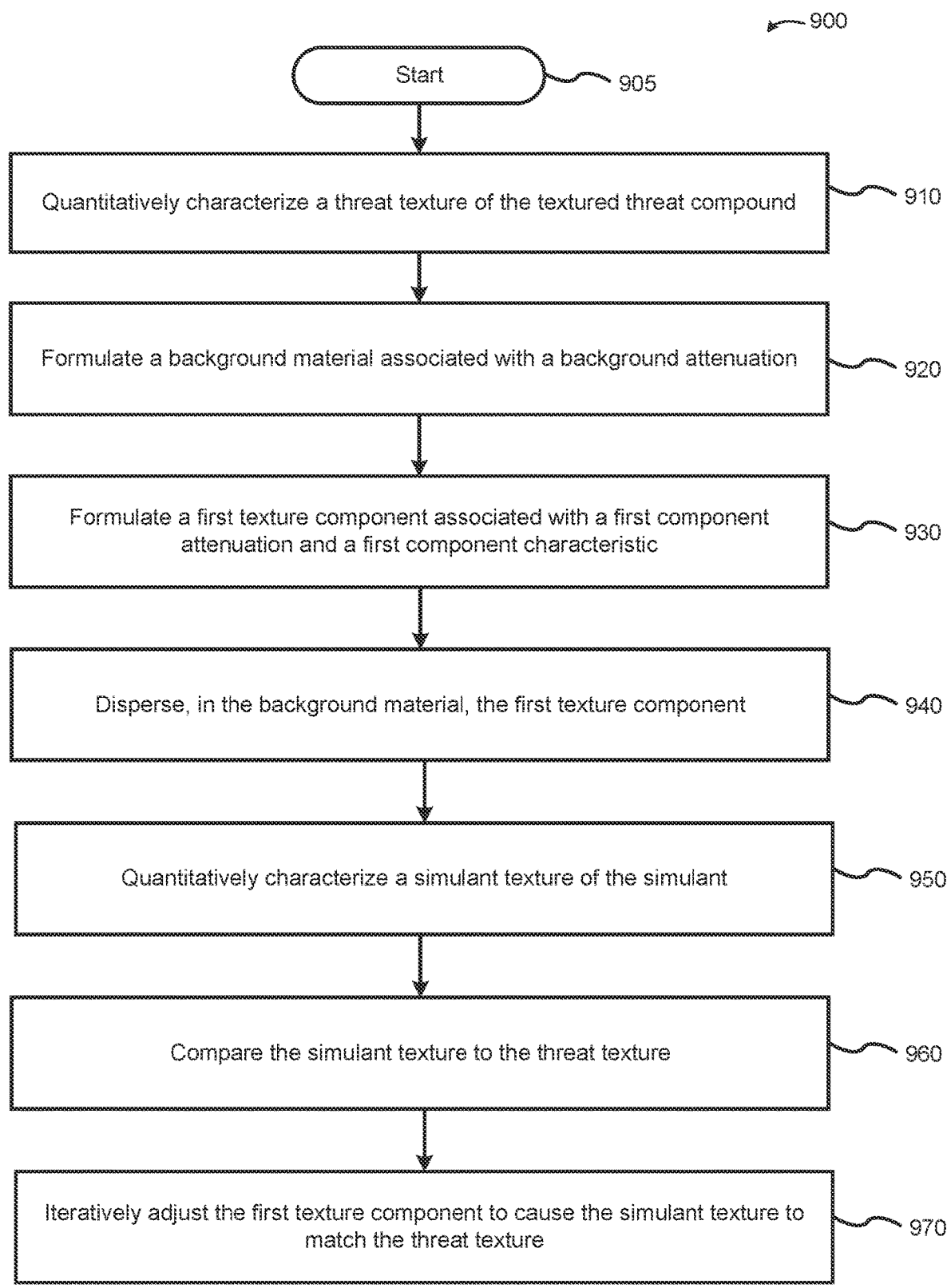
FIG. 9 illustrates another method of producing a simulant of a textured threat compound according to an example embodiment.

FIG. 9 illustrates another method 900 of producing a simulant of a textured threat compound according to an example embodiment. The method starts at block 905. In block 910, a threat texture of the textured threat compound is quantitatively characterized. For example, the textured threat compound can be scanned to acquire at least one threat image; the background and texture components of the image are identified; the grayscale values of the background and texture components are characterized; and component characteristic(s) of the texture components are identified. Example approaches include 1) thresholding, followed by segmentation to identify particles, and 2) gray level co-occurrence matrices.

In block 920, a background material associated with a background attenuation is formulated. For example, a formulation is developed by matching a morphology property and an X-ray property of a background of the textured threat compound.

In block 930, a texture component(s) associated with component attenuation(s) and component characteristic(s) is formulated. For example, a wax formulation exhibiting the component attenuation can be developed to match a high-attenuation characteristic of a textured component of the textured threat compound; the wax formulation can be melted and cast into a solid block that is then mechanically separated into particles; and the particles can be sieved according to a plurality of particle size bins spanning a range of particle sizes of the high-attenuation characteristic of the textured component of the textured threat compound. In an alternate example, an aggregate formulation exhibiting component attenuation to match a low-attenuation characteristic of a textured component of the textured threat compound is developed; the aggregate formulation is fused by compression via vacuum suction fusion to achieve a semi-solid morphology of the aggregate formulation; the solid block is mechanically separated into particles; and the particles are sieved according to a plurality of particle size bins spanning a range of particle sizes of the low-attenuation characteristic of the second textured component of the textured threat compound.

In block 940, the texture component(s) is dispersed in the background material, e.g., by mixing, stirring, or otherwise mechanically combining the texture component(s) with the background material. A desired dispersion (e.g., a dispersion consistent with a target characteristic/distribution) can be accomplished by controlling an intensity and/or duration of the process of combining the ingredients.

In block 950, a simulant texture of the simulant is quantitatively characterized, e.g., using scanning and analytical analysis with an image processing algorithm or tool.

In block 960, the simulant texture is compared to the threat texture, e.g., by quantifying various characteristics of the simulant and threat, such as morphology, grayscale (micro-CT), CTN high, CTN low, Ze, Pe, or other characteristics that can include distributions or other characterizations of non-homogenous aspects In block 970, the texture component(s) is iteratively adjusted to cause the simulant texture to match the threat texture. For example, a relative contribution by weight of a given texture component can be adjusted to vary its overall percent by weight of the resulting simulant compared to the background material(s) or other component(s). The distribution characteristics of a given texture component can be varied, e.g., by adjusting how the component is achieved by using different approaches to breaking into pieces, or sieving, or various other adjustments to the component. Furthermore, it is possible to adjust the duration or intensity of the mixing to vary the distribution characteristics of the component in the overall mixture producing the simulant.

While a number of example embodiments have been described, it should be appreciated that the present invention provides many applicable inventive concepts that can be embodied in a wide variety of ways. The example embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure and the knowledge of one of ordinary skill in the art.

Terms and phrases used in this document, unless otherwise expressly stated, should be construed as open ended as opposed to closed—e.g., the term "including" should be read as meaning "including, without limitation" or the like; the term "example" is used to provide example instances of the item in discussion, not an exhaustive or limiting list thereof; the terms "a" or should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Furthermore, the presence of broadening words and phrases such as "one or more," "at least," "but not limited to," or other similar phrases, should not be read to mean that the narrower case is intended or required in instances where such broadening phrases may be absent. Any headers used are for convenience and should not be taken as limiting or restricting. Additionally, where this document refers to technologies that would be apparent or known to one of ordinary skill in the art, such technologies encompass those apparent or known to the skilled artisan now or at any time in the future.

What is claimed is:

1. A method of iteratively adjusting grayscale values of formulations as visualized by micro computed tomography (micro-CT) explosives detection systems (EDS), comprising:
    scanning a textured threat compound using a micro computed tomography (micro-CT) explosives detection system (EDS) to obtain a 3-dimensional image of threat texture component particles of the textured threat compound;
    removing a visual background from the 3-dimensional image of the textured threat compound by setting a threshold to remove pixels having a pixel value less than the lowest value of the threat texture component particles;
    quantitatively characterizing a threat texture of the textured threat compound as revealed in the 3-dimensional image after removing the background, including a size, shape, and distribution of the threat texture component particles having sufficient size and preponderance that can be identified and used in explosive detection;
    characterizing attenuating properties of a candidate background material with the micro-CT EDS to visualize its grayscale value, on a scale of 0 to 255, on an output of the micro-CT EDS;
    formulating a first texture component formulation separate from the candidate background material by adding, to the candidate background material, a candidate wax to thereby increase an attenuating property of the first texture component formulation as characterized by the micro-CT EDS;
    scanning the first texture component formulation with the micro-CT EDS to visualize a first texture component grayscale value, on the scale of 0 to 255, on an output of the micro-CT EDS;
    adjusting the first texture component grayscale value by iteratively adding more candidate wax and scanning until the first texture component formulation, as visualized by the micro-CT EDS relative to the background material, displays an average grayscale value in the range of approximately 60 to 80 levels higher relative to the grayscale value of the candidate background material, the first texture component grayscale value indicating that the first texture component formulation is associated with a first component attenuation different than attenuation of the candidate background material;
    consolidating the first texture component formulation to produce a consolidated first texture component formulation;
    mechanically separating the consolidated first texture component formulation into first texture component particles according to a first component characteristic;
    dispersing, in the candidate background material, the first texture component particles according to the first component characteristic;
    quantitatively characterizing a simulant texture of the simulant comprising the background material including the first texture component particles dispersed therein, by scanning the simulant in the micro-CT EDS to observe the first component characteristic;
    comparing the simulant texture to the threat texture as characterized by the micro-CT EDS including size, shape, and distribution of texture component particles of the simulant texture and threat texture having sufficient size and preponderance that can be identified and used in explosive detection; and
    iteratively dispersing the first texture component particles into the background material to adjust the first component characteristic of the first texture component, and quantitatively characterizing the simulant texture, until the simulant texture has a non-homogeneous dispersion of attenuation that matches an irregularity size and preponderance of the threat texture to within a range corresponding to being generally visually indistinguishable from dispersion of attenuation of the threat texture when viewing scanning results.

2. The method of claim 1, wherein quantitatively characterizing the threat texture comprises:
    scanning the textured threat compound to acquire at least one threat image;
    identifying a background component and texture components of the at least one threat image based on differing grayscale values visualized in the at least one threat image of the background component and texture components;
    characterizing grayscale values of the texture components; and
    identifying a first component characteristic of the texture components, for use in mechanically separating the first texture component formulation, which is consolidated.

3. The method of claim 2, further comprising:
    sieving the particles of the first texture component according to a plurality of particle size bins spanning a range of particle sizes of a high-attenuation characteristic of the textured component of the textured threat compound.

4. The method of claim 1, further comprising formulating a second texture component and dispersing, in the background material, the second texture component, wherein formulating the second texture component comprises:

adding, to the candidate background material, the candidate wax to thereby increase an attenuating property of a second texture component formulation as characterized by the micro-CT EDS;

scanning the second texture component formulation with the micro-CT EDS to visualize a second texture component grayscale value on an output of the micro-CT EDS;

adjusting the second texture component grayscale value by iteratively adding more candidate wax and scanning until the second texture component formulation, as visualized by the micro-CT EDS, displays an average grayscale value in the range of approximately 20-30 levels higher relative to the grayscale value of the candidate background material, the second texture component formulation thereby being associated with a second component attenuation relatively higher than the background attenuation and relatively lower than the first component attenuation;

fusing the second texture component formulation by compression via vacuum suction fusion to achieve a semi-solid morphology of the second texture component formulation;

mechanically separating the second texture component formulation into second texture component particles;

sieving the second texture component particles according to a plurality of particle size bins spanning a range of particle sizes of a second component characteristic; and dispersing, in the candidate background material containing the first texture component particles, the second texture component particles according to the second component characteristic.

5. The method of claim 1, wherein consolidating the first texture component formulation comprises melting and casting the first texture component into a solid.

6. The method of claim 1, wherein consolidating the first texture component formulation comprises fusing the first texture component formulation by compression via vacuum suction fusion to achieve a semi-solid morphology.

* * * * *